United States Patent [19]

Kleiss

[11] 4,057,995
[45] Nov. 15, 1977

[54] APPARATUS AND METHOD FOR MEASURING LOW BOILING COMPONENT CONTAINED IN RELATIVELY HIGH-BOILING LIQUID

[75] Inventor: Louis D. Kleiss, Borger, Tex.

[73] Assignee: Phillips Petroleum Company, Bartlesville, Okla.

[21] Appl. No.: 577,138

[22] Filed: May 13, 1975

[51] Int. Cl.² .............................................. G01N 7/00
[52] U.S. Cl. ............................................ 73/23; 203/1
[58] Field of Search ............... 73/23, 19, 25, 53, 64.2; 203/1, 2, 91; 201/1

[56] References Cited

U.S. PATENT DOCUMENTS

| | | | |
|---|---|---|---|
| 2,645,949 | 7/1953 | De Boisblanc | 73/64.2 |
| 2,880,611 | 4/1959 | Herren | 73/53 |
| 3,108,929 | 10/1963 | Tolin et al. | 73/23 |
| 3,145,561 | 8/1964 | Thompson | 73/64.2 |
| 3,191,428 | 6/1965 | Piros | 73/64.2 |
| 3,221,541 | 12/1965 | Osborne | 73/53 |
| 3,332,856 | 7/1967 | Hart | 73/64.2 |
| 3,342,700 | 9/1967 | Rijnsdrop | 203/1 |
| 3,521,478 | 7/1970 | Magorien | 73/19 |
| 3,528,440 | 9/1970 | Plucker | 73/64.2 |

Primary Examiner—Jerry W. Myracle
Assistant Examiner—Stephen A. Kreitman

[57] ABSTRACT

An apparatus and method are provided for measuring the concentration of a light hydrocarbon in a relatively high boiling liquid mixture. A chamber is sealed liquid full of the liquid mixture. The internal volume of the chamber is then increased by mechanical means, causing the liquid to boil adiabatically within the chamber. The absolute pressure within the chamber is then measured and indicates the amount of light hydrocarbon present as compared to previous samplings. In a specific embodiment of the invention the apparatus comprises a chamber with a spring and bellows mechanism for increasing the internal volume of the chamber. In a further embodiment of the invention the input of heat to a distillation column is controlled in response to a signal generated corresponding to the absolute pressure measured in a continuous sequential sampling of liquid from a chosen point within the distillation column.

7 Claims, 2 Drawing Figures

SAMPLE VALVE A INLET
TOP VENT VALVE B
BOTTOM VENT VALVE C
AIR INJECTED INTO BELLOWS VALVE D
☐ (VENTS TO ATMOS)
RELAY 21 CLOSES, SWITCH E, OUTPUT READ

APPARATUS AND METHOD FOR MEASURING LOW BOILING COMPONENT CONTAINED IN RELATIVELY HIGH-BOILING LIQUID

BACKGROUND OF THE INVENTION

This invention relates to ddetermining the concentration of a light hydrocarbon in a relatively high boiling liquid mixture. In one of its aspects this invention relates to the absolute vapor pressure attributable to the adiabatic expansion of a light hydrocarbon in a mixture in its relationship to the relative amount of light hydrocarbon in the mixture. In another of its aspects this invention relates to a mechanical apparatus suitable for increasing the internal volume of a closed chamber. In yet another of its aspects this invention relates to the control of the heat input to a distillation process in response to the continuous sampling and determination of the relative amount of light hydrocarbon within sequential samples taken from the distillation process.

In one of its concepts this invention relates to an apparatus and method for measuring the absolute pressure within a chamber upon expansion of a liquid sample containing light hydrocarbon in a relatively high boiling liquid mixture with the variation in pressure between sequential samples being used as control for the reboiler heat input to the distillation process.

In many extractive distillation or liquid-liquid extraction processes a solvent is used to selectively absorb a light hydrocarbon from a mixture of other light hydrocarbons. The light hydrocarbon-rich solvent is then distilled to remove the desired light hydrocarbon and the lean solvent is cooled and recycled to the extraction process. The efficiency of the extraction process is greatly impaired if light hydrocarbon is not completely removed from the recycled solvent. Typically, the recycled, lean solvent should contain less than .01 weight percent of the light hydrocarbon.

Some typical extraction processes using the system above are the extraction of butadiene from a stream comprising butadiene and butenes using a solvent comprising one of the following as the primary component: (a) furfural, (b) dimethylformamide, (c) high boiling glycols such as di- and triethylene glycol, (d) ethers of such high boiling glycols and the like. Other extraction processes include separations in which high boiling compounds such as esters, ethers, sulfolane, and similar compounds are employed as solvents.

The extraction of butadiene, butene-1, butene-2, n-butane, isobutane, isoprene, propane and the like from mixtures comprising these compounds using appropriate solvents are examples of the systems to which my procedure is applicable. The extraction of aromatics such as benzene, toluene, etc., from paraffins is another example of suitable extraction systems.

Efforts have been made in the past to control the removal of a light hydrocarbon such as butadiene from a solvent such as a mixture of furfural, oils and water, by using temperature control of the lower part of the distillation column. Results have been unreliable because non-ideal distillation is encountered, with the distillation non-idealities changing in an unpredictable manner with pressure, temperature, and concentration ratios. Because of these non-idealities, tray temperature is not a reliable guide for controlling the light hydrocarbon content of the solvent. Lacking an adequate method of measurement and control it has been common practice to overstrip, i.e., to remove light hydrocarbon more completely from the solvent than is warranted by the economics of the process. This overstripping wastes both solvent and energy. In many processes the application of excess heat can cause polymerization of the solvent thereby losing some of the solvent and possibly damaging equipment by polymer laydown.

It is, therefore, an object of this invention to provide an apparatus and method for process measurement and control in which a sample stream is withdrawn from a non-linear distillation process, such as the stripping of butadiene from a solvent mixture of furfural, oils and water, to be tested for absolute vapor pressure at a temperature lower than existing at the sample point. It is a further object of the invention to provide apparatus and method for automatically and continuously measuring the absolute vapor pressure of the liquid sample stream and applying the results obtained in sequential sampling to control of the process from which the samples are withdrawn.

Other aspects and objects of this invention will become apparent upon reading the disclosure and the appended claims.

STATEMENT OF THE INVENTION

It has been discovered that a good correlation exists between the light hydrocarbon content and the absolute vapor pressure of a vapor sample of the hydrocarbon drawn from a lower tray of a solvent stripper distillation column. This sample is condensed and the vapor pressure is measured at 75°–95° F. Using this discovery a method is provided for measuring the concentration of a light hydrocarbon dissolved in a relatively high boiling liquid mixture. A sample chamber of this invention is flow purged with liquid sample and the chamber is closed-in liquid full then the internal volume of the chamber is mechanically increased so that part of the liquid vaporizes adiabatically. The absolute pressure within the chamber is then measured and in a sequence of samples variation of the absolute pressure indicates variation in the relative amount of light hydrocarbon in the samples.

In a specific embodiment of the invention a specific apparatus has been provided in which within the sample chamber a bellows is sealed to the chamber so that the exterior of the bellows forms an interior wall of the chamber with the bellows being acted upon by a spring so that the bellows is at least partially collapsed by the spring. A means is provided for supplying gas pressure to the interior of the bellows to counteract the collapsing pressure of the spring so that upon removal of the gas pressure the spring acts to collapse the bellows thereby increasing the internal volume of the chamber.

In another embodiment, a sequencing timer coupled with appropriate electrical and electromechanical devices is used to repeatably program a sequence of purging, sealing, expansion, and absolute pressure measurement with signal generation and holding, so that a continuous sequence of output signals is produced responsive to the variation of absolute vapor pressure of repeated liguid samplings.

In a further embodiment of the invention a signal is produced in response to the measurement of the absolute vapor pressure of a process sample stream and is used to control the heat input to the distillation process from which the sample stream is taken. Sequential variation of the signal generated in response to sequential sampling varies the heat input to the process.

The invention can best be understood in conjunction with the drawings which will be described in a process for the stripping of butadiene from a solvent comprising furfural, oils and water.

Figure 1:
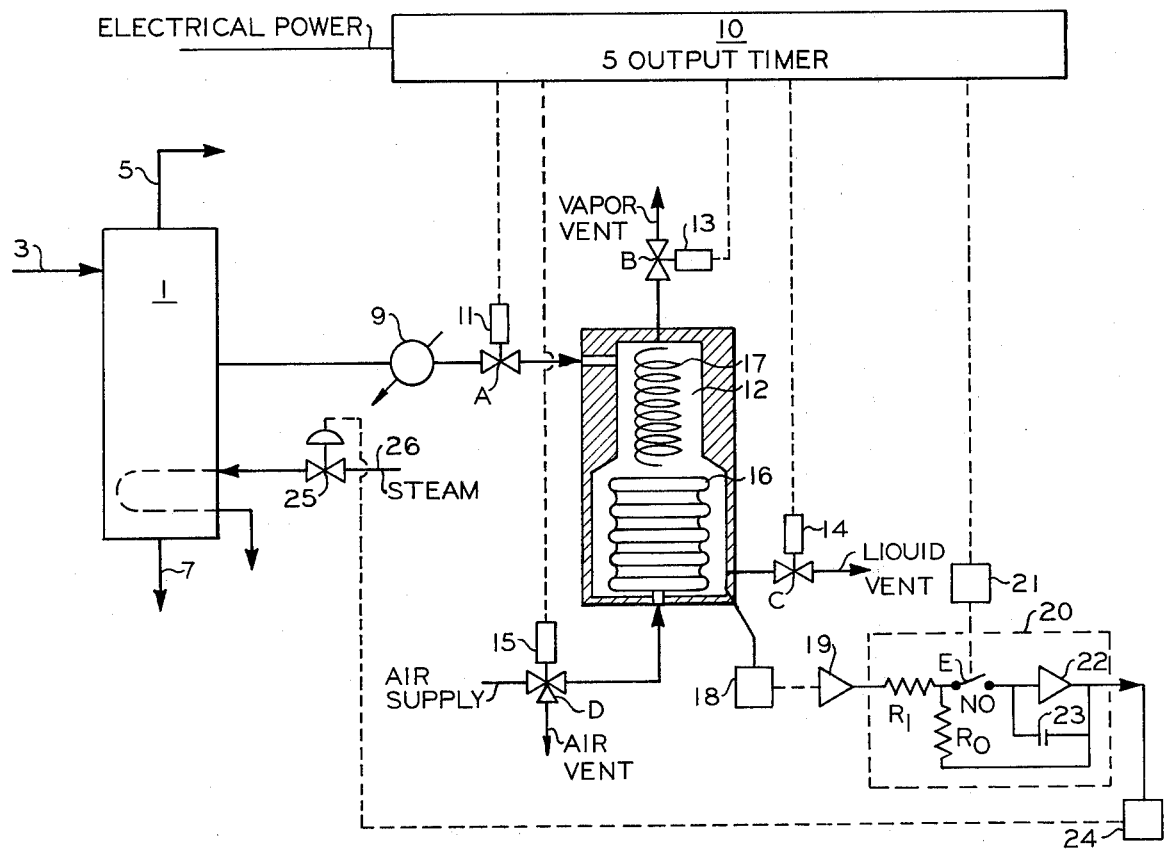
FIG. 1 is a schematic drawing showing an apparatus for the absolute pressure measurement of a continuous liquid sample from a distillation column and generation of a control signal to control heat input to the column.

Referring now to FIG. 1 of the drawing, I have built and applied an apparatus to measure the absolute vapor pressure of a condensed vapor sample from the stripping section of a distillation column in which butadiene is stripped from a solvent mixture of water, furfural and oils obtained in an extraction process. The partial pressure of a typical condensed vapor sample is estimated as follows.

The term "oils" used in the specific example includes butadiene dimer, butadiene trimer and other reaction products formed by butadeine and furfural during the extraction step.

Water — 22 mm of mercury
Furfural — 8 mm of mercury
Oils — 30 mm of mercury
Butadiene — about 125 mm per mol %

A continuous vapor sample is drawn, for instance, from the 12th tray of a 40 tray distillation column 1 operated at about 60 psig with inlet feed 3, butadiene overhead 5 and solvent bottoms 7. The temperature of this tray is about 285° F. The vapor sample is cooled to 75°–85° F in condenser 9, whereupon it liquefies and separates into aqueous and oily phases. The oily phase contains nearly all of the butadiene in the sample. Periodically, a portion of this flowing sample, primarily the oily phase, is sealed liquid full into a chamber. While it remains sealed, the volume of this chamber is increased 1–5 percent by mechanical means. The liquid boils adiabatically, producing vapor to fill the void created by the volume increase. The absolute pressure of the chamber is then measured, and this pressure is representative of the absolute vapor pressure of the sample. It has been found that a typical 12th tray condensed vapor sample of a furfural stripper has an absolute vapor pressure of 150–250 mm of mercury. This measurement, when made on line using the apparatus described below, can be used to control the steam heat in line 26 supplied to the distillation column 1. Such control may be manual or automatic, according to well-known control techniques.

Timer 10 can be a continuous motor driven cam timer having five electrical switch closures. Cams are adjustable so that each switch can be programmed to make or break at any given point in the timer cycle. The five dashed lines extending from timer 10 represent electrical circuits carrying power to five actuating coils. Solenoid valve 11 opens to admit sample to measurement caivty 12 when electrical power is applied, closes when power is cut off. Solenoid valves 13 and 14 similarly open to vent the top and bottom, respectively, of the cavity when electrical power is applied. A three ported solenoid valve 15 admits air pressure to bellows 16 when power is applied, expanding the bellows against spring 17, thus shrinking the internal volume of measurement cavity 12. When power is removed from valve 15 coil, valve D vents bellows 16 air to atmosphere, and spring 17 collapses the bellows 16, thus expanding the internal volume of cavity 12. Mechanical stops are provided to limit the longitudinal travel of the bellows and the springs in both directions. The stiffness of spring 17, the working area of bellows 16, the internal volume of cavity 12, and air pressure are chosen so that when air is applied to bellows 16, the internal volume of cavity 12 will decrease a definite percentage in the range of 1–5 percent, and when air is vented the cavity will return to original volume. Further, this increase/-decrease in volume is repeatable whether the cavity is being flushed by sample flow under pressure, or is under vacuum in measurement.

Transducer 18 and electronic preamplifier 19 are shown connected by a dashed line which represents interconnecting cable. Transducer 18 is an absolute pressure measurement transducer connected to cavity 12. It can be of a strain gage type. Electronic preamplifier 19 provides excitation current to transducer 18 and amplifies the transducer output. It has zero and span adjustments, and produces an output voltage in the range of 0–10 volts DC. This voltage is related to the absolute pressure of cavity 12 and is suitable for actuating commercial indicating, recording, and process control instruments.

The circuit shown enclosed in dashed line box 20 is a schematic of a typical voltage follower and clamping circuit. When the actuating coil of relay 21 receives power from timer 10, the switch E contacts will close. If $R_i = R_o$, amplifier 22 output will assume the same voltage as the output of electronic preamplifier 19. When relay 21 opens switch E again under the command of timer 10, capacitor 23 will cause amplifier 22 to hold (clamp) this voltage until switch E closes again. In the figure the output of amplifier 22 is fed to means 24 in which a control signal is generated which controls steam inlet valve 25 on the reboiler of column 1 admitting steam through line 26 to supply heat to the column.

Figure 2:
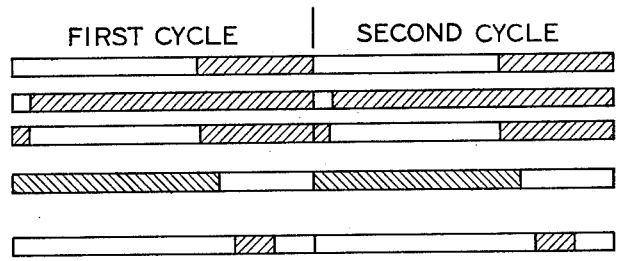
FIG. 2 is a graphic representation showing the sequence from left to right of electrical power outputs from timer 10 to the various valve and switch actuating coils and describes the operating status of the apparatus during the portions of the time cycle.

FIG. 2 is a graphic representation showing the sequence from left to right of electrical power outputs from timer 10 to the various valve and switch actuating coils. It should be considered in relationship to FIG. 1. FIG. 2 also describes the operating status of the apparatus during the portions of the time cycle. The length of the time cycle is optional, usually 0.5 to 8 minutes. It should be emphasized that the last sample flow through the cavity before it is shut in is in a downward direction from the top of cavity 12 to the bottom of the cavity. In this manner, liquid in the cell is predominately the lighter, oil phase, containing nearly all of the butadiene. The transducer output is read after valve D is opened to the atmosphere, allowing the spring to collapse the bellows 16 thus expanding the internal volume of cavity 12. Considering a time cycle of 8 minutes for the obtaining of a single reading, it can be seen from FIGS. 1 and 2 how a sample is injected into cavity 12 and a reading taken. At the start valves A and B are open. This allows the sample to enter cavity 12, with the gas venting through valve B at the top of the cavity. The sample will be injected through Valve A for about 5 minutes, after which valve A is closed. The sample is vented through B for ½ minute and then valve B is closed for the remaining 7½ minutes. At the end of the first ½ minute, bottom valve C opens, allowing the excess sample which flows into cavity 12 to vent through the bottom of the cavity, with valve C being closed at the end of 4½ minutes. The operation of valves B and C allows cavity 12 to fill with liquid from the top down. During all the time that the sample has been injected, air has been injected into the bellows through valve D, keeping it in an expanded position. At the end of 5½ minutes, relay 15 opens valve D to vent. This action allows the atmospheric pressure to be the only pressure exerted in cavity bellows 16. Thus the spring is allowed to compress the bellows in accordance with this invention. This operation allows for increase in volume in cavity 12. Adiabatic vaporization of the fluid in the chamber occurs. It is now possible to obtain the absolute pressure reading of the pressure within cavity 12 which occurs at the end of 6 minutes, due to the action of relay 21 closing the switch E to amplifier 22. Switch E is kept closed for 1 minute, after which it is opened, providing a new signal to amplifier 22 which is held as a clamped signal in amplifier 22 by condenser 23 until the completion of a second cycle which begins 1 minute after switch E is opened. The new signal from amplifier 22 is applied to controller 24 to adjust controller valve 25 to increase or decrease the amount of steam going through line 26. One minute after switch E is opened, a new cycle is started as shown in FIG. 2. This absolute pressure measurement is somewhat sensitive to the temperature of the sample and measurement apparatus. Sufficient accuracy is achieved by locating the apparatus in a temperature controlled room. However, if it is desired to provide temperature compensation, a selected negative temperature coefficient resistor (e.g., thermistor) can be placed in temperature equilibrium with the measurement cavity of the apparatus and electrically connected in series with $R_o$, shown in FIG. 1. Alternately, a selected positive temperature coefficient resistor (e.g., silicon) can be placed in temperature equilibrium with the measurement cavity and electrically connected in series with $R_i$, also shown in FIG. 1. A combination of these compensation methods may be used.

While this apparatus has been described as applied to measurement and control of a furfural stripper, it can also be used to measure and control other non-ideal distillation processes, particularly where the component of interest is low boiling as compared to the other components.

I claim:
1. An apparatus for measuring the concentration of light hydrocarbon in a relatively high boiling liquid, said apparatus comprising:
   a. a liquid-tight chamber having an inlet means and means for purging with liquid sample;
   b. within the chamber (1) a bellows sealed to the chamber so that the exterior of the bellows forms an interior wall of the chamber and (2) a spring acting on the bellows at least partially to collapse the bellows;
   c. a means for supplying gas pressure to the interior of the bellows to counteract the collapsing pressure of said spring;
   d. in communication with the interior of the chamber a means for measuring the absolute pressure within the chamber; and
   e. means for maintaining a constant temperature surrounding said chamber.

2. An apparatus of claim 1 further comprising means for generating a signal corresponding to the absolute pressure within the chamber.

3. An apparatus of claim 2 further comprising (1) means for continuously sampling an operating distillation column, (2) transmitting said sample to said chamber in a timed sequence, and (3) means for controlling the heat input to said operating distillation column in response to said signal corresponding to the absolute pressure within the chamber.

4. A method for measuring the concentration of a light hydrocarbon in a relatively high boiling liquid mixture comprising:
   a. flow purging with a liquid comprising light hydrocarbon in a relatively high boiling liquid under conditions of constant temperature a liquid-tight chamber having a bellows sealed to the chamber so that the exterior of the bellows forms an interior wall of the chamber and a spring acting on the bellows at least partially to collapse the bellows;
   b. maintaining sufficient pressure within said bellows to counteract the collapsing pressure of said spring;
   c. maintaining said chamber in liquid full, liquid-tight isolation;
   d. removing pressure from within the bellows so that the bellows is partially collapsed by the spring thereby increasing the internal volume of the chamber; and
   e. after adiabatic vaporization of liquid within the chamber measuring the absolute pressure within the chamber.

5. A method of claim 4 for generating a signal corresponding to the concentration of a light hydrocarbon in a relatively high boiling liquid further comprising generating a signal corresponding to the absolute pressure within the chamber.

6. A method of claim 5 for controlling the heat input to an operating distillation column comprising (1) continuously sampling an operating distillation column, (2) transmitting said sample to said chamber in a timed sequence, and (3) controlling the heat input to said operating distillation column in response to the sequential signals corresponding to the absolute pressure measured within the chamber.

7. A method of claim 6 wherein the light hydrocarbon is butadiene and the relatively high boiling liquid is a mixture of furfural, water and oils.

* * * * *